United States Patent [19]

Hata et al.

[11] Patent Number: 5,769,780
[45] Date of Patent: Jun. 23, 1998

[54] METHOD OF MANUFACTURING NATURAL TISSUE VALVES HAVING VARIABLY COMPLIANT LEAFLETS

[75] Inventors: Cary Hata, Alhambra; Roger Tu, Tustin, both of Calif.; Hsing-Wen Sung, Taipei, Taiwan; Shih-Hwa Shen, Irvine, Calif.

[73] Assignee: Baxter International Inc., Deerfield, Ill.

[21] Appl. No.: 948,365

[22] Filed: Oct. 9, 1997

Related U.S. Application Data

[60] Continuation of Ser. No. 646,801, May 21, 1996, abandoned, which is a division of Ser. No. 300,025, Sep. 2, 1994, Pat. No. 5,549,666.

[51] Int. Cl.⁶ .............................. A61F 2/24; A61F 2/04; A61L 17/00
[52] U.S. Cl. .................................. 600/36; 623/2; 623/12; 623/901; 8/94.11
[58] Field of Search .................... 623/2, 11, 12, 623/901; 8/94.11; 600/36

[56] References Cited

U.S. PATENT DOCUMENTS

| Re. 31,035 | 9/1982 | Hancock et al. . | |
|---|---|---|---|
| 3,709,175 | 1/1973 | Edwards et al. . | |
| 3,966,401 | 6/1976 | Hancock et al. | 8/94.11 |
| 4,050,893 | 9/1977 | Hancock et al. | 8/94.11 |
| 4,182,446 | 1/1980 | Penny . | |
| 4,247,292 | 1/1981 | Angell | 8/94.11 |
| 4,350,492 | 9/1982 | Wright et al. . | |
| 4,364,127 | 12/1982 | Pierce et al. . | |
| 4,372,743 | 2/1983 | Lane . | |
| 4,477,930 | 10/1984 | Totten et al. . | |
| 4,624,822 | 11/1986 | Arru et al. | 623/2 |
| 4,629,459 | 12/1986 | Ionescu et al. . | |
| 4,648,881 | 3/1987 | Carpentier et al. . | |
| 4,798,611 | 1/1989 | Freeman, Jr. . | |
| 4,800,603 | 1/1989 | Jaffe . | |
| 5,080,670 | 1/1992 | Imamura et al. | 623/2 |
| 5,116,564 | 5/1992 | Jansen et al. . | |
| 5,352,240 | 10/1994 | Ross . | |
| 5,376,110 | 12/1994 | Tu et al. | 623/1 |
| 5,500,014 | 3/1996 | Quijano et al. . | |
| 5,549,666 | 8/1996 | Hata et al. | 623/2 |

FOREIGN PATENT DOCUMENTS

| 0 065 827 A1 | 12/1982 | European Pat. Off. . |
|---|---|---|
| 0 084 395 A1 | 7/1983 | European Pat. Off. . |
| 0 402176 | 12/1990 | European Pat. Off. . |
| 2 399 832 | 3/1979 | France . |
| 2 046 165 | 11/1980 | United Kingdom . |
| 2 063 675 | 6/1981 | United Kingdom . |
| 2 143 306 | 2/1985 | United Kingdom . |
| 2 169 386 | 7/1986 | United Kingdom . |

*Primary Examiner*—Paul B. Prebilic
*Attorney, Agent, or Firm*—Raymond Sun; Guy L. Cumberbatch

[57] ABSTRACT

Variably compliant natural tissue valve leaflets and vascular bioprosthetics incorporating variably compliant leaflets are provided along with methods for their manufacture. The variably compliant leaflets are fixed with the leaflet base section under greater pressure than the leaflet tip section rendering them relatively stiff along the leaflet base section and more flexible at the leaflet tip section. The radially variable flexing characteristics of the valve leaflets promote even distribution of mechanical stress on the valve assembly during the cardiac cycle leading to improved hemodynamic performance while retarding the calcification of the leaflet tissue.

36 Claims, 2 Drawing Sheets

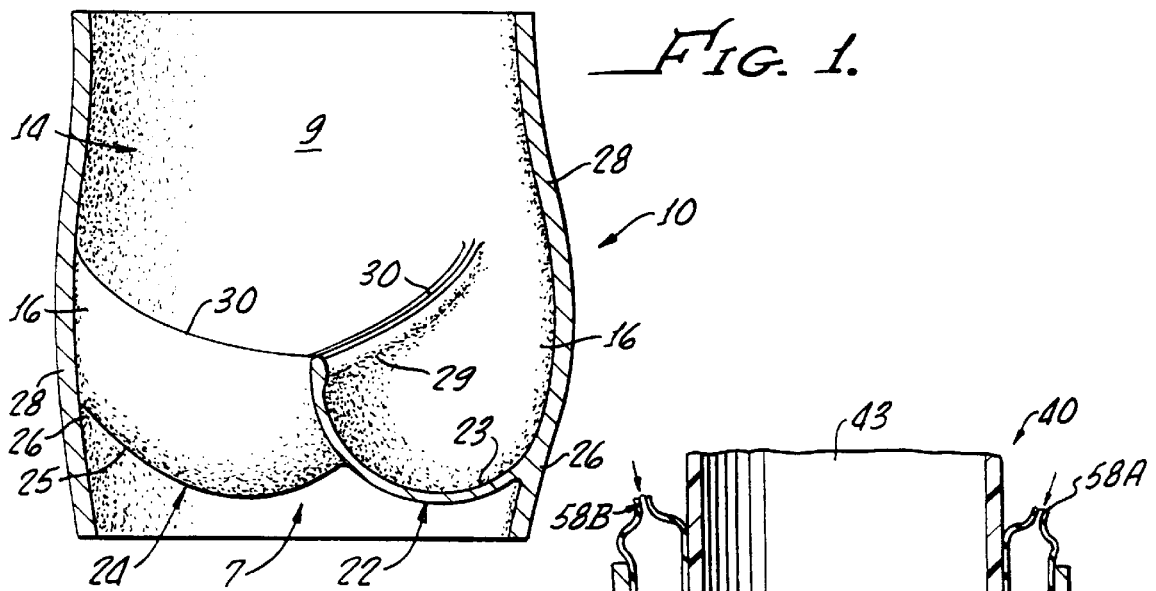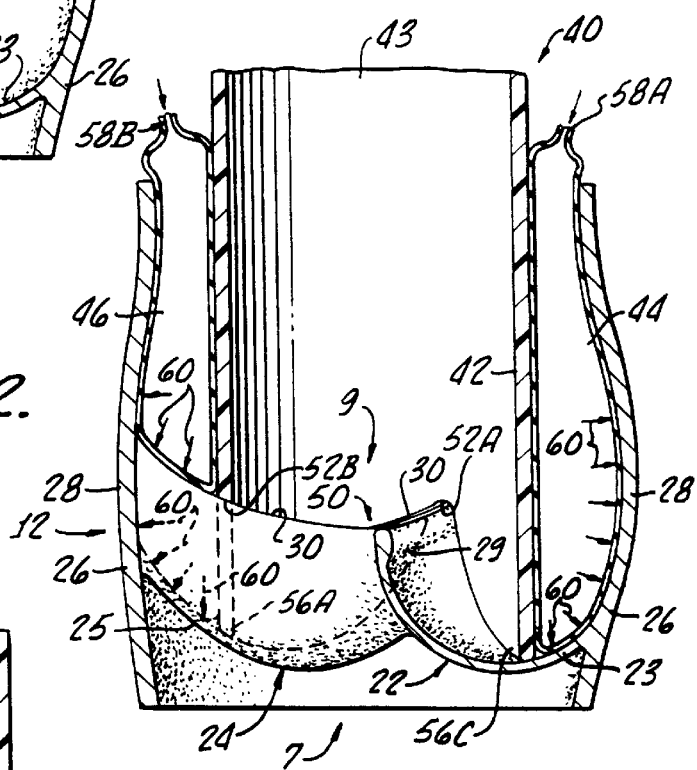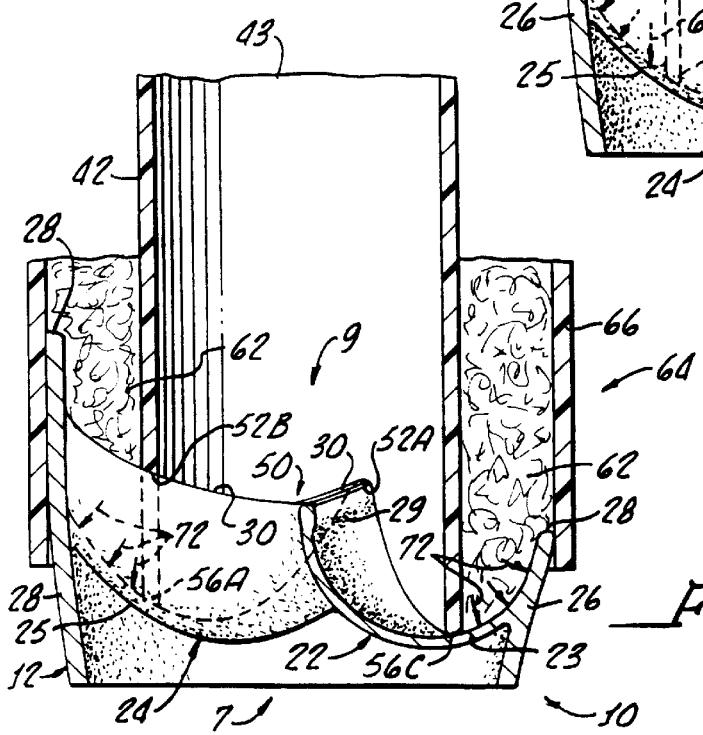

METHOD OF MANUFACTURING NATURAL TISSUE VALVES HAVING VARIABLY COMPLIANT LEAFLETS

This application is a continuation of U.S. application Ser. No. 08/646,801 filed May 21, 1996 and now abandoned, which is a divisional application of U.S. application Ser. No. 08/300,025 filed Sep. 2, 1994, now U.S. Pat. No. 5,549,666.

FIELD OF THE INVENTION

The present invention relates to tissue valve prostheses and to methods for their manufacture and use. More particularly, this invention relates to natural tissue valvular prosthetic devices with variably compliant valve leaflets providing improved hemodynamic characteristics and enhanced durability.

BACKGROUND OF THE INVENTION

A variety of pathological processes can lead to valvular malfunction in a mammalian cardiovascular system.

This is particularly true of the valves found in the heart which are essential for controlling the flow of blood.

Natural tissue heart valves are thin, fibrous structures having substantial tensile strength. Primarily composed of collagen proteoglycans and small amounts of elastin, natural tissue heart valves are flexible and variably compliant yet durable. Among other causes, heart valve deterioration may be brought about by genetic diseases of the connective tissues where crosslinking of collagen is impaired, by rheumatic fever, and by a variety of infectious diseases. Valve dysfunction is usually associated with degenerative changes of the valve tissue that require surgical correction or replacement with a bioprosthetic device. While artificial or mechanical bioprostheses have been used for some time they continue to present problems including clot formation and excessive turbulence following implantation.

These and other deficiencies associated with mechanical valvular prosthetics have spurred the development of heart valve substitutes incorporating naturally-occurring valve structures. In one form, these prostheses are constructed using allografts, that is tissue from human corpse aortic valves. However, a shortage of human donors and the possibility of pathogenic contamination have limited the use of cadaveric allografts. Accordingly, xenogeneic valvular prostheses, i.e., those based on tissue from a species other than human, have become the principal form of valve replacement implanted today. Typically, xenogeneic valve prostheses are manufactured from bovine pericardium or porcine heart valves which closely resemble human valve structures and, less frequently, from membranes of dura mater (cranial membranes) or fascia lata (connective tissue) from cattle.

Yet, when tissue is transplanted directly from the source organism, it rapidly deteriorates in the hostile physiological environment of the host. It was quickly established that "fixation" of the natural tissue is critical to the operation of implanted tissue valves for prolonged periods. Glutaraldehyde or polyepoxy compounds have become the most common agents for fixing tissue used in valvular prosthetics. In addition to arresting autolysis, the fixing agents produce a stronger, more resilient material having improved tensile properties due to increased collagen crosslinking. Crosslinking of the collagen molecules also increases their resistance to proteolytic cleavage thereby rendering the treated tissue less susceptible to enzymatic degradation in the body. Further, fixing agents have the ability to reduce the antigenicity of xenograft tissue to a level at which it can be implanted into the heart without provoking a significant immunological reaction from the host.

From a clinical standpoint, long term tissue damage in fixed valvular prosthetics is primarily the consequence of destruction of the collagen fiber network, calcification, and shearing forces occurring from obstructions in the valve orifice area. Calcification is the single largest cause of failure in biological valvular prosthetics, whether they incorporate pericardial valve leaflets or natural valve structures. Commonly, the buildup of calcium requires the replacement of the prosthetic device after a few years, subjecting the patient to substantial risk.

Conventional fixation techniques tend to increase the rate of calcification by making the valve tissue uniformly stiff and noncompliant. Like tanned shoe leather, uniformly stiff valve tissue and, in particular, valve leaflets lead to an uneven distribution of applied stress. Unlike living valve tissue which is variably compliant, that is having radially asymmetric flexing characteristics along the leaflet body, uniformly stiff fixed leaflets do not distribute dynamic strain homogeneously throughout the tissue matrix. As with a shoe, the irregular distribution of force and the resulting stress points produce localized tearing, cracking and abrasion. The accumulation of calcium is accelerated where the non-compliant connective tissue is subjected to repetitive motions that increase the amount of matrix disruption and detached fibers. In addition to enhancing the rate of calcification due to the disruption of the tissue matrix at these stress points, inhibition of the variably compliant motions of the prosthetic leaflets can lead to stenosis, increased fluid turbulence, and an elevated rate of tissue abrasion in and around the prosthetic device.

Accordingly, while prior art fixation techniques substantially improve the characteristics of the treated tissue, problems still remain with respect to shape retention, elasticity, strength, calcification and durability. Simple immersion of the valve tissue into a bath of fixative subjects it to random hydrostatic or hydrodynamic forces resulting in uniformly stiff leaflets that are not variably compliant. The uniform stiffness and decreased compliance promotes incorrect architecture and undesirable strain concentrations throughout the tissue when introduced into a physiological setting.

In order to overcome these limitations, several attempts have been made to fix the valvular tissue under pressure. Fixing the valvular structure under constant pressure can reinforce its natural configuration and help assure the proper coaptation of the valve leaflets following implantation. Examples of constant pressure fixation processes may be found in U.S. Pat. Nos. 3,983,581, 4,035,849 and 4,050,893 in which porcine valves are fixed in glutaraldehyde with the valve cusp held in a closed position by applying hydraulic pressure to the ventricular or outflow side of the valve. The selected pressure is uniformly maintained over the entire surface of the ventricular side of the valve establishing a pressure differential across the width of the leaflet.

Despite improvements in terms of the initial architectural configuration, tissue leaflets treated under pressurized conditions are still uniformly stiff rather than variably compliant. As with unpressurized fixation techniques, the elimination of variable flexibility increases the uneven stress on the tissue matrix which, in turn, enhances the rate of calcification. Again the resulting calcium crystal formation interferes with the natural collagen biomechanics, hemodynamic flow and detracts from the ability of the valve to maintain its precise architecture during years of service.

Accordingly, it is an object of the present invention to produce a natural tissue valve prosthesis with variably compliant leaflets having improved hemodynamic performance.

It is another object of the present invention to produce a natural tissue valve prosthesis wherein the valve leaflets are resistant to calcification.

It is still another object of the present invention to provide a natural tissue prosthetic devices having enhanced durability and a correspondingly longer performance profile following implantation.

SUMMARY OF THE INVENTION

These and other objectives are achieved by the present invention which, in a broad aspect, is directed to natural tissue valvular bioprosthetics having variably compliant valve leaflets and to methods for their production and use. More particularly the present invention provides a novel tissue fixation process which may be used to produce valve leaflets that are variably compliant, exhibiting radially asymmetric flexing characteristics along the leaflet body. Preferably, the valve leaflets will be fixed so as to provide a relatively stiffer base section adjacent to the annular margin of the valve assembly and a relatively flexible tip section adjacent to the commissures of the valve assembly. This radial flexibility gradient along the valve leaflet allows it to move much more harmoniously in response to the flow of blood than valve leaflets fixed using traditional methods.

Moreover, the asymmetric flexibility of the valve leaflets tends to lower the in vivo pressure gradient necessary to open the valve while reducing the pressure drop and turbulence across the valve structure. These improved hemodynamic properties result in a much more even distribution of mechanical stress across the tissue matrix of the leaflet thereby retarding the calcification of the leaflet tissue and associated deterioration of the prosthetic device.

Valve leaflets are made variably compliant during the fixation procedure of the present invention by subjecting different sections of each individual leaflet to different contact forces resulting in pressure. Preferably the leaflet base, that is the section of the valve leaflet closer to the circumferential valvular margin or annulus, is chemically fixed while subjected to relatively high pressure. At the same time, the leaflet tip section closer to the commissures is exposed to chemical fixatives under relatively low pressure. The application of compressive force or pressure to a localized area during fixation increases the amount of cross-linking within the tissue matrix at that locale and compacts the fibrous protein structure, thereby increasing the local stiffness of the valve leaflet.

At the base section of the leaflet, the application of relatively higher pressure assures a degree of cross-linking and matrix compression that renders the leaflet stiffer and less compliant. In contrast, the tip section of the leaflet is subjected to little or no compressive force or pressure and is therefore extremely flexible providing each leaflet of the valve assembly with the desired flexibility gradient. This flexibility gradient in the leaflet tissue makes valvular assemblies fixed in this manner more harmonically compliant than valve leaflets fixed under uniformly low pressure.

Other objects, features and advantages of the present invention will be apparent to those skilled in the art from a consideration of the following detailed description of preferred exemplary embodiments thereof taken in conjunction with the figures which will first be described briefly.

BRIEF DESCRIPTION OF THE DRAWINGS

FIG. 1 is a longitudinal sectional view of an excised porcine aortic valve showing the valve leaflets of the valve assembly;

FIG. 2 is a longitudinal sectional view of an excised aortic valve arranged in an exemplary fixation apparatus with the leaflet base sections subject to contact force from pressure bladders according to the present invention;

FIG. 3 is a longitudinal sectional view of an excised aortic valve arranged in an exemplary fixation apparatus with the leaflet base sections subject to contact force from soft porous packing material;

DETAILED DESCRIPTION OF EXEMPLARY EMBODIMENTS

Figure 4:
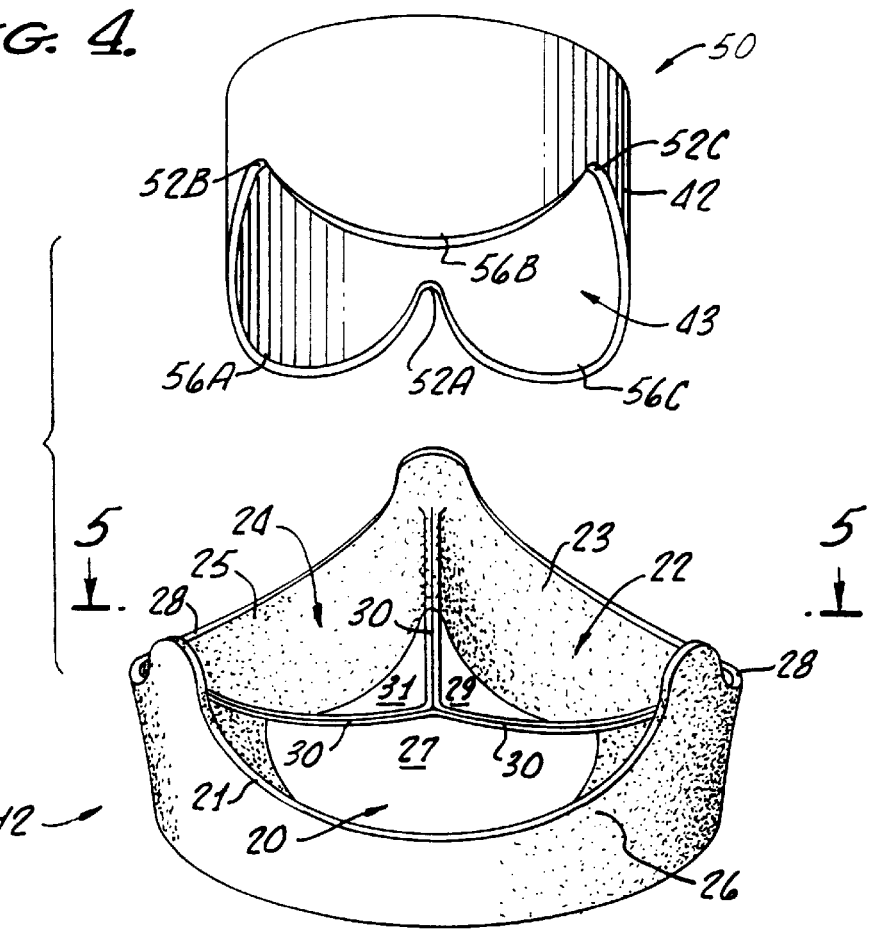
FIG. 4 is an exploded perspective view illustrating a fixed porcine aortic valve assembly in a diastolic configuration and a fixation apparatus in accordance with the present invention.

Any natural tissue prosthetic valve assembly may be fabricated in accordance with the teachings of the present invention. For example, the variable pressure fixation process as of the present invention may be used to produce prosthetic devices designed to replace venous valved conduits, aortic valves, pulmonary valves, mitral valves or tricuspid valves. Similarly, the present invention is not limited to a particular valve assembly configuration and may be used in valvular prosthetics with or without stents, sewing rings, annuloplasty rings, or other support frames. Further, the present invention may be used in connection with heterologous, homologous or autologous natural tissue valve leaflets including those derived from xenogeneic valve assemblies, pericardial tissue or connective tissue and membranes such as fascia lata and dura mater.

However, since aortic valves are more likely to require repair than are pulmonary or other valvular structures, the following discussion is directed to the fabrication of an exemplary variably compliant aortic bioprosthesis. Moreover, as porcine aortic valves are widely used to form bioprosthetic devices, this exemplary discussion is directed to this xenogeneic valvular tissue, it being understood that the principles discussed with respect to the treatment and replacement of porcine aortic valves apply equally to other natural tissue sources. Accordingly, the present invention is not restricted to the formation of xenogeneic aortic prosthetic devices, but may be practiced to produce any natural tissue valvular prostheses having two or more leaflets.

Turning now to the Figures, FIG. 1 illustrates a sectional view of an aortic heart valve and associated tissue, generally designated 10, which has been excised from a pig or other suitable xenogeneic source. For convenience, the entire aortic root is removed and later surgically modified for implantation. During normal operation blood flows from inflow side 7, shown at the bottom of FIG. 1, of aortic valve 10, through valve assembly 12 to outflow side 9 which is shown at the top of FIG. 1. Valvular assembly 12, shown in its closed or diastolic position, has been excised along with a section of the ascending aorta 14 and processed to remove extraneous tissue including aortic tissue above the sinuses of valsalva 16, the annulus and subvalvular structures (not shown). Valvular assembly 12 includes three valve cusps or leaflets 20, 22, 24 as shown more clearly in the corresponding plan view of FIG. 5. Each of the three valve leaflets 20, 22, 24 is attached to annular margin 26 of aortic wall 28 adjacent to their respective leaflet base section 21, 23, 25. The exterior of aortic wall 28, has preferably been surgically modified to provide a thickness of approximately 1 mm. Valve leaflets 20, 22, 24 are attached so as to pivot about annular margin 26 when subjected to hemodynamic forces. The circumference of annular margin 26 substantially conforms to the scalloped shape of the sinuses of valsalva 16 which are disposed in aortic wall 28 immediately above.

Figure 5:
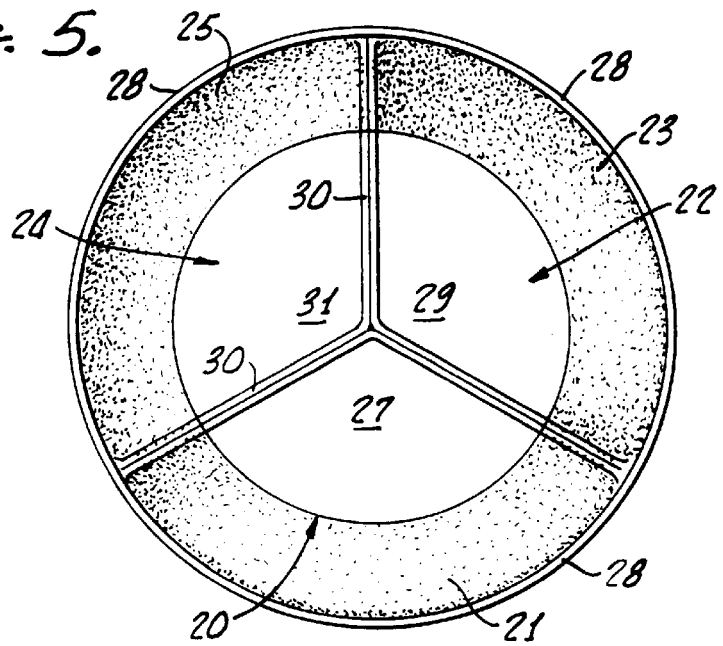
FIG. 5 is a top plan view taken along section line 5—5 in FIG. 4.

Leaflets 20, 22, 24 are shown in the closed or diastolic position and, when viewed from the outflow side 9 as in FIG. 5, exhibit the coming together or coaptation of free leaflet borders adjacent to leaflet tip sections 27, 29, 31 at commissures 30. As the heart muscle contracts, forcing blood through valvular assembly 12, valve leaflets 20, 22, 24 deform and pivot upward about annular margin 26 to assume an open or systolic position with the free leaflet borders of commissures 30 positioned some distance apart. As previously discussed conventional fixation techniques provide valve leaflets that do not deform uniformly during contraction thereby leading to uneven stress distribution and incomplete opening. In any case, the heart muscle once again expands and the resulting increase in fluid pressure exerted on the outflow surface of leaflets 20, 22, 24 forces them downward into the diastolic position with the commissures 30 again coapted ready for the next cardiac cycle.

After aortic valve 10 has been correctly sized, trimmed and burped, preferably under moisture rich conditions, it is positioned in a valve fixation apparatus to be processed according to the teachings of the present invention. Aortic valve 10 may be sized and trimmed as desired as long as valve assembly 12 including leaflets 20, 22 24 and annular margin 26 are left intact. Various valve holders or valve storage devices having different configurations may be used to hold valve assembly 12 during the variable fixation procedure. Moreover, prior to being placed in the valve fixation apparatus, aortic valve 10 or valvular assembly 12 may be mounted or otherwise affixed to a stent, sewing ring or other structure using known techniques. Commonly, this optional supporting member is affixed annularly to the inflow side of valvular assembly 12 so as not to interfere with the natural movements of valve leaflets 20, 22, 24.

One exemplary fixation apparatus is shown in FIG. 2 and designated generally as 40. In the embodiment shown, fixation apparatus 40 includes relatively rigid central tube 42, shown more clearly in FIG. 4, and pressure bladders 44, 46. A third pressure bladder, arranged circumferentially equidistant from the other two with respect to central tube 42, is not shown in the Figures but acts in the same manner as pressure bladders 44, 46. Central tube 42 extends longitudinally from outflow side 9 of valve assembly 12 and is generally cylindrical in nature defining a bore 43, and a tube end portion 50. Central tube 42 may be of any diameter smaller than the inner diameter of aortic valve wall 28 adjacent to the outflow side of annular margin 26.

Preferably, tube end section 50 of central tube 42 has a plurality of inverted U-shaped incisions extending upward from the outflow side of valve leaflets 20, 22, 24 corresponding to the number of commissures in the valve assembly to be fixed. The incisions define axially projecting arcuate segments interspersed between them. For example, in the embodiment shown in FIG. 2, central tube 42 has three incisions 52A, 52B, 52C, defining arcuate segments 56A, 56B, 56C. Tube end section 50 along with incisions 52A, 52B, 52C and arcuate segments 56A, 56B, 56C is more clearly seen FIG. 4 where central tube 42 is not in contact with valve assembly 12. When in place as in FIG. 2, incisions 52A, 52B, 52C receive raised commissures 30 thus allowing arcuate segments 56A, 56B, 56C of tube end section 50 to bias valve leaflets 20, 22, 24 into a closed or diastolic position. A conventional supporting member (not shown), affixed as discussed above or unattached may be used to hold valve assembly 12 adjacent to central tube 42.

Following the positioning of central tube 42 contacting valve leaflets 20, 22, 24, pressure bladders 44, 46, preferably in a deflated condition, are placed between the outer wall of central tube 42 and the inner surface of aortic wall 26. Alternatively, pressure bladders 44, 46 may be attached to the outer wall of central tube 42 so as to assume the desired configuration when central tube 42 is properly positioned. In either case, pressure bladders 44, 46 and a third pressure bladder (not shown) are substantially aligned with arcuate segments 56A, 56B, 56C of central tube 42. In this position end portions 54A, 54B, of pressure bladders 44, 46 are adjacent to leaflet base sections 23, 25. At the same time valve leaflet tip sections 27, 29, 31 extend upwardly into bore 43, sequestered from pressure bladders 44, 46 by the relatively rigid wall of central tube 42. The third pressure bladder is similarly positioned with respect to leaflet base section 21 and, for the purposes of the following discussion, acts in an identical manner as pressure bladders 44, 46.

After determining that valve assembly 12 is correctly positioned in the fixation apparatus or holder, and the coaption of commissures 30 remains intact, the entire assembly is submerged in a fixation solution incorporating one or more fixing agents. The immersion is sufficient to expose all surfaces of the valve assembly to the fixing agents. It is important to note that valve assembly 12 may be also be positioned in the holder or fixation apparatus while already immersed in the liquid fixative. The order of these steps is not critical as long as the valve assembly is maintained in a moistened state during positioning so as to prevent tissue damage through desiccation.

The variable pressure fixation process of the present invention is compatible with conventional fixing agents and may be practiced using standard fixative concentrations and exposure times. For example, agents such as polyepoxy compounds, glutaraldehyde, formaldehyde and other aldehydes may be used, alone or in combination, to fix the leaflet tissue matrix. Preferably, polyepoxy compounds or glutaraldehyde are used during the fixation procedure rather than formaldehyde which is more likely to degrade the valve tissue. Exemplary fixation solutions which work particularly well include 0.2% aqueous glutaraldehyde at a pH of about 7.4 and 4% EX-313, a glycerol polyglycidyl ether composition (Nagase Chemicals Ltd. Osaka, Japan) at an approximate pH of 8.0 to 11.0. Moreover, during the fixation cycle, the concentration of the fixation solution may be varied. For example, in the case in which solutions of glutaraldehyde are used, an initial pre-fixation step may be performed using a solution of glutaraldehyde having concentration on the order of 0.2% which increases to a final concentration on the order of 0.5% during subsequent fixation steps. Of course, as will be readily appreciated by those skilled in the art, other fixing agents and concentrations may be utilized at the discretion of the practitioner.

As with conventional fixation protocols, the exposure time may range from a few hours to several days depending on the composition of the fixation solution, degree of crosslinking desired and source of tissue used for the valve leaflet. The exposure time to fixation solutions is generally termed a fixation cycle. Generally, fixation cycles are determined by the period required to permanently establish the geometry and dimensions of the valvular assembly. In one exemplary embodiment, the valve assembly was submersed in a polyepoxy fixation solution for approximately six days. Yet, fixation cycles may be shortened to a matter of hours by increasing the concentration of fixative or raising the temperature of the solution to between approximately 35° C. to 45° C. Following variable pressure fixation, the valve leaflets or valve assembly are integrated into finished prosthetic devices and stored under standard conditions until ready for use.

During immersion in the fixation solution, pressure is selectively applied to discrete sections of the valve leaflets through contact force. In the embodiment shown in FIG. 2 this pressure, represented by force arrows 60, is applied to leaflet base sections 23, 25 by inflating pressure bladders 44, 46. At the same time, the third pressure bladder will be inflated to apply pressure to leaflet base section 21. Inflation media, which may be liquid or gas, is injected through inflation ports 58A, 58B to fill pressure bladders 44, 46 thereby expanding them as desired. The expansion of pressure bladders 44, 46 within the confined space defined by the relatively rigid outer surface of central tube 42, the inner surface of aortic wall 28 and the outflow surface of valve leaflets 22, 24 imparts a contact force resulting in pressure on all of these surfaces.

Most significantly, force arrows 60 illustrate the application of pressure to the outflow surface of leaflet base sections 23, 25 which are held in place through the tensile strength of the leaflet tissue and annular margin 26. The contact area over which the pressure or contact force is applied is not fixed and may be altered by changing the diameter of central tube 42 or the expanded configuration of pressure bladders 44, 46. Typically, leaflet base sections 21, 23, 25 and the corresponding contact area may extend anywhere from 5% to 80% of the length of the leaflet measured radially from annular margin 26 to the leaflet tip. While the desired pressure is applied to leaflet base sections 21, 23, 25, leaflet tip sections 27, 29, 31 are sequestered within bore 43 and are subjected to little or no pressure.

The application of pressure to the tissue matrix is highly selective with respect to the amount of contact force employed and limited to discrete sections of the leaflet surface. For example, when fixing an intact valve assembly, the contact force is preferably applied to the outflow side of the valve leaflets to bias them in their naturally closed position thereby promoting shape retention and coaptation following implantation. While the contact force is applied to the outflow side of the valve leaflets in the illustrated embodiments, it is clearly within the scope of the invention to apply the desired pressure to the selected sections of the leaflets from the inflow side. Moreover, when fixing pericardial tissue or membranes from fascia lata or dura mater, contact force may be applied to either face or both sides simultaneously if desired.

Force is preferably applied using a solid surface to directly contact the leaflet where increased stiffness is desired. However, force may be applied using liquid or air assuming it is properly confined. Depending on the extent of the leaflet section to be subjected to pressure, the force may be applied to a point, line or discrete area on the tissue surface. In FIG. 2 the solid contacting surface corresponds to the exterior surface of pressure bladders 44, 46 when expanded. The amount of force employed is selected to provide the desired stiffness to the area of the leaflet being contacted and may range from less than half a gram to approximately one hundred grams. The precise force applied will vary depending on such factors as the fixing agent used, time of exposure to the fixation solution and area of the leaflet contacted. Moreover, in accordance with the teachings of the present invention, different pressures may be applied to leaflet tip sections 27, 29, 31 and leaflet base sections 21, 23, 25 simultaneously. Under such conditions the pressure applied to the leaflet tip section is less than the pressure applied to the leaflet base section ensuring that the leaflet tip section is relatively more flexible that the leaflet base section. Accordingly, as with the base sections, the force which may be applied to the leaflet tip sections 27, 29, 31 can range from less than half a gram to approximately 100 grams. The desired force to the base sections and tip sections may either be applied statically or intermittently, taking place during all or part of the fixation cycle.

FIG. 3 illustrates another embodiment of the present invention where contact force is applied to a valvular assembly 12 using a soft porous material 62 rather than pressure bladders. In this embodiment, aortic valve 10 is essentially the same as shown in FIGS. 1 and 2 except that the outflow section of aortic wall 28, including sinuses of Valsalva 16, have been surgically excised. While the ascending aorta has been removed, valve assembly 12, including annular margin 26 with valve leaflets 20, 22, 24 pivotally attached, is left intact. As with the valve assemblies previously discussed, valve leaflet tip sections 27, 29, 31 come together defining commissures 30. A portion of aortic wall 28 is also left intact on the inflow side of valve assembly 12. Other components are the same as those shown in FIG. 2, so that the corresponding parts are designated by the same reference numerals and their descriptions are omitted.

Surgically modified aortic valve 10 is positioned in valve fixation apparatus 64 prior to the initiation of the fixation procedure. As with valve fixation assembly 40 shown in FIGS. 1 and 2, valve fixation apparatus 64 includes a central tube 42 defining a bore 43. However, valve fixation apparatus 64 further includes peripheral tube 66 oriented axially with central tube 42 and having an inner diameter as large or larger than the outer diameter of annular margin 26. Accordingly, valve assembly 12 is placed within peripheral tube 66, with or without a supporting member (not shown) adjacent to the inflow side of valve leaflets 20, 22, 24. Central tube 42 is positioned adjacent to the outflow surface of valve leaflets 20, 22, 24 as previously described. Incisions 52A, 52B, 52C, are aligned to receive raised commissures 30 thereby allowing arcuate segments 56A, 56B, 56C of tube end section 50 to bias valve leaflets 20, 22, 24 into a closed or diastolic position. In this configuration leaflet tip sections 27, 29, 31 extend into bore 43.

Following the placement of valvular assembly 12 in fixation apparatus 64, an innocuous packing material 62 is introduced into the axial cavity defined by the outer wall of central tube 42 and the inner wall of peripheral tube 66 to contact leaflet base sections 21, 23, 25. Packing material 62 is desirably porous and capable of absorbing the fixation solution so that good contact between the valve leaflet and fixing agent is achieved. Accordingly, packing material 62 may be formed of any natural or manmade substance which is preferably soft and pliant so as not to damage the leaflet tissue. Moreover, packing material 62 may exhibit a certain amount of elastic memory or coefficient of expansion to facilitate contact with the leaflet tissue and promote an even distribution of force over the desired area. Exemplary materials that are compatible with the teachings of the present invention include natural or artificial sponges, natural or artificial fabrics, and resilient polymeric foams. Preferably the material chosen does not react with the fixing agent or agents and will not degrade or leach into the fixation solution.

The selected material may optionally be soaked in fixation solution prior to being placed in contact with valve leaflets 20, 22, 24. In any case, packing material 62 is introduced to the opening between the tubes 42 and 66 and pushed down inside aortic wall 28 until contact is made with the outflow surface of leaflet base sections 21, 23, 25. Typically, packing material 62 will also contact the surface of tubes 42 and 66. Yet, as long as the desired contact force is applied to valve leaflets 20, 22, 24, the amount of packing material 62 used is not critical and may be adjusted on a case by case basis. The amount of force applied to the selected leaflet section, represented in FIG. 3 by arrows 72, may range from less than a gram to approximately one hundred grams depending on the stiffness desired and the particulars of the fixation cycle employed. Moreover, as with the other embodiments discussed, contact force 72 may be applied intermittently, sinusoidally, continuously or in combinations thereof throughout the fixation cycle by appropriate adjustments to packing material 62. More generally, packing material 62 may be contacted or removed from the surface of valve leaflets 20, 22, 24 at any time during the fixation cycle.

It will be appreciated by those skilled in the art that the variable pressure fixation process of the present invention may be practiced using any fixation apparatus that allows force to be applied to a selected section of the valve leaflet. For example, there is no requirement that a fixation apparatus used to produce variably compliant valve leaflets incorporate either a central tube, peripheral tube or their equivalents. Rather, variably compliant leaflets may be produced in accordance with the present invention using nothing more than conventional wire frame valve holders and a solid surface to contact the desired section of the leaflet tissue. Moreover, when the valve leaflets are to be fabricated from membrane tissue, variable pressure fixation may be performed using nothing more than two solid surfaces. This ability to use a wide variety of commercially available valve holders and other fixation equipment simplifies the procedure while at the same time increasing efficiency in terms of cost and labor.

The effectiveness of the present invention is further illustrated by the following nonlimiting example.

EXAMPLE I

A porcine aortic heart valve was isolated, trimmed and burped according to techniques well known in the art. The valve was then mounted on a conventional fixation apparatus having an annular frame adjacent to the outflow surface of the valve leaflets. When mounted, the valve leaflets were biased so as to assume a diastolic or closed position.

Subsequent to mounting the trileaflet valvular assembly, a soft, round porous sponge was soaked in fixation solution and inserted at the outflow sinus in between the wire frame of the holder, aortic wall and the base section of the valve leaflet. This process was then repeated for each of the other two valve leaflets. Upon placement of the sponges, it is estimated that the force exerted on each leaflet base section was less than one gram. The base leaflet contact area adjacent to the annular margin of the valve assembly extended approximately one-third of the length of the leaflet when measured radially from base to tip.

Following the application of pressure to the selected sections of the leaflet surfaces, the entire holder-valve combination was immersed in a aqueous fixation solution of 4% Denacol® polyepoxy compound EX-313, a glycerol-polyglycidyl ether (Nagase Chemicals Ltd., Osaka, Japan). Prior to immersion, the pH value of the fixation solution was adjusted to approximately 9.0 using NaOH or HCl. The valvular assembly was then fixed at room temperature for a period of six days.

Upon removal, the hemodynamic characteristics of the variably compliant leaflets were tested. It was found that the asymmetrically compliant leaflets, fixed according to the teachings of the present invention, moved much more harmonically than porcine leaflets fixed under uniformly constant pressure conditions. Moreover, the valve assembly with variably compliant leaflets exhibited a much lower transvalvular pressure gradient and less corresponding turbulence than did heart valves fixed under constant pressure conditions.

FIGS. 4 and 5 show a porcine aortic valvular assembly 12 fixed according to the present invention. FIG. 4 also shows tube end section 50 of central tube 42 with incisions 52A, 52B, 52C aligned so as to receive commissures 30 thereby allowing arcuate segments 56A, 56B, 56C to contact valve leaflets 20, 22, 24. Leaflet base sections 21, 23, 25 are shown as shaded areas arranged circumferentially adjacent to annular margin 26. During the fixation cycle, leaflet base sections 21, 23, 25 have been exposed to contact force as described above and are relatively stiff. In contrast, leaflet tip sections 27, 29, 31, which are shown as non-shaded leaflet areas in FIGS. 4 and 5, were positioned in central bore 43 during the fixation cycle and subjected to little or no contact force. Accordingly, valve leaflets 20, 22, 24 are asymmetrically compliant, varying radially from the leaflet tip to the leaflet base.

The asymmetrically or variably compliant leaflets may be stored and prepared for implantation using standard techniques. For example, valve assembly 12 may be immersed in saline or other non-reactive solutions in the same apparatus used during the fixation cycle. Prior to implantation, valve assembly 12 may be further trimmed or attached to a stent or sewing ring if desired. Alternatively, valve assembly 12 may be affixed directly to the patient's annulus. Of course, when variably compliant leaflets are produced individually rather than as part of a valvular assembly, it will be necessary to incorporate them in a suitable prosthesis before implantation.

In either case, upon implantation variably compliant leaflets 20, 22, 24 will move harmonically with the natural hemodynamic pulsations of the heart. Relatively stiff leaflet base sections 21, 23, 25 adsorb and distribute most of the energy valve assembly 12 is subjected to at the start of the systolic phase of cardiac cycle. As a result, compliant leaflet tip sections 27, 29, 31 will experience lower stress levels which are more evenly distributed across the leaflet tissue. This allows the compliant leaflet tip sections to react sinusoidally to the hemodynamic flow passing through annular margin 26 thereby reducing the pressure gradient and corresponding turbulence. The asymmetric compliance ensures that stress imparted by the movement of valve leaflets 20, 22, 24 is radially distributed in an even manner from leaflet base sections 21, 23, 25 to leaflet tip sections 27, 29, 31 eliminating stress concentrations and inhibiting the calcification of the tissue. This reduction and uniform distribution of stress also occurs at the beginning of the diastolic phase of the cardiac cycle when increased pressure on the outflow surfaces of valve leaflets 20, 22, 24 forces them into a closed position.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the present invention.

What is claimed is:

1. A process for fixing a natural tissue valve prosthesis having improved hemodynamic characteristics and resistance to calcification, said process comprising:
   (a) obtaining a mammalian natural tissue valve assembly having a circumferential annular margin and one or more valve leaflets pivotally attached to said circumferential annular margin, each of said one or more valve leaflets including a leaflet base section adjacent to said circumferential annular margin and a leaflet tip section disposed radially therefrom;
   (b) subjecting each of said leaflet base sections of said one or more valve leaflets to a higher pressure than each of said leaflet tip sections on the same side of the valve leaflet; and
   (c) contacting each of said sections of said pressurized natural tissue valve assembly with a fixing agent.

2. The process of claim 1 wherein each of said leaflet base sections comprises from approximately 5% to approximately 80% of the length of each of said one or more valve leaflets measured radially from said circumferential annular margin.

3. The process of claim 1 wherein said fixing agent is selected from the group consisting of polyepoxy compounds, glutaraldehyde, formaldehyde and combinations thereof.

4. The process of claim 2 wherein said fixing agent is a polyepoxy compound and said polyepoxy compound is glycerol-polyglycidyl ether.

5. The process of claim 1 wherein said tissue valve assembly is selected from the group consisting of tri-leaflet valve assemblies and bileaflet valve assemblies.

6. The process of claim 1 wherein said pressure is applied intermittently to said valve leaflet while said natural tissue valve assembly is contacted with said fixing agent.

7. The process of claim 1 wherein said natural tissue valve assembly is a porcine valve assembly.

8. The process of claim 1 wherein said pressure is derived from contact force applied by a soft porous material.

9. A process for fixing a natural tissue valve leaflet having improved hemodynamic characteristics and resistance to calcification, said process comprising:
   (a) providing a natural tissue valve leaflet having a leaflet base section and a leaflet tip section disposed adjacent thereto;
   (b) subjecting said leaflet base section to a higher pressure than said leaflet tip section on the same side of the valve leaflet; and
   (c) contacting each of said sections of said pressurized natural tissue valve leaflet with a fixing agent.

10. The process of claim 9 wherein said fixing agent is selected from the group consisting of polyepoxy compounds, glutaraldehyde, formaldehyde and combinations thereof.

11. The process of claim 10 wherein said fixing agent is a polyepoxy compound and said polyepoxy compound is a glycerol-polyglycidyl ether.

12. The process of claim 8 wherein said natural tissue valve leaflet is derived from tissue selected from the group consisting of pericardial tissue, fascia lata membrane, and dura mater membrane.

13. The process of claim 1, wherein step (b) includes the step of retaining said leaflet base sections and said leaflet tip sections in separate chambers during the application of higher pressure to said leaflet base sections.

14. The process of claim 7, wherein step (b) includes the step of retaining said leaflet base sections and said leaflet tip sections in separate chambers during the application of higher pressure to said leaflet base sections.

15. The process of claim 1, wherein the leaflet base sections are subjected to a pressure created by contact with a solid body.

16. The process of claim 15, wherein the solid body is an exterior surface of a pressure bladder.

17. A process as in claim 1, further including positioning a rigid tube adjacent an outflow side of the valve leaflets, the tube being concentric with and spaced inwardly from the annular margin, wherein said step of subjecting comprises applying said higher pressure to the leaflet base sections outside of said tube.

18. A process as in claim 17, wherein the higher pressure is applied to said leaflet base sections by inflating a bladder positioned outside of the tube.

19. A process as in claim 18, wherein the natural tissue valve assembly being fixed is a tri-leaflet valve, and the process further includes providing three discrete bladders outside of the tube adjacent each leaflet for applying the higher pressure to said leaflet base sections.

20. A process as in claim 1, further comprising mounting the natural tissue valve prosthesis on a surrounding stent support prior to said step of subjecting.

21. The process of claim 9, wherein the leaflet base sections are subjected to a pressure created by contact with a solid body.

22. The process of claim 21, wherein the solid body is an exterior surface of a pressure bladder.

23. A process as in claim 9, further including positioning a rigid tube adjacent an outflow side of the valve leaflets, the tube being concentric with and spaced inwardly from the annular margin, wherein said step of subjecting comprises applying said higher pressure to the leaflet base sections outside of said tube.

24. A process as in claim 23, wherein the higher pressure is applied to said leaflet base sections by inflating a bladder positioned outside of the tube.

25. A process as in claim 24, wherein the natural tissue valve assembly being fixed is a tri-leaflet valve, and the process further includes providing three discrete bladders outside of the tube adjacent each leaflet for applying the higher pressure to said leaflet base sections.

26. A process as in claim 9, further comprising mounting the natural tissue valve prosthesis on a surrounding stent support prior to said step of subjecting.

27. A process for fixing a natural tissue valve prosthesis having an annular margin and a plurality of leaflets extending generally radially inwardly from the margin, comprising:
   securing the margin from movement;
   positioning a tubular member concentrically within the margin and in contact with the leaflets on a downstream side thereof so as to bias the leaflets into a closed position, the tubular member being sized smaller than the margin so that a base section of each leaflet is exposed on the downstream side between the margin and tubular member and a tip section of each leaflet is disposed within the tubular member; and
   subjecting the base section of the leaflets to a higher pressure than the tip section while contacting the natural tissue valve prosthesis with a fixing agent.

28. The process of claim 27, wherein the leaflet base sections are subjected to said higher pressure created by contact with a solid body.

29. A process as in claim 28, wherein the higher pressure is applied to said leaflet base sections by inflating a bladder positioned outside of the tubular member.

30. A process as in claim 29, wherein the natural tissue valve assembly being fixed is a tri-leaflet valve, and the process further includes providing three discrete bladders outside of the tubular member adjacent each leaflet for applying the higher pressure to said leaflet base section.

31. A process as in claim 27, wherein the tubular member includes three axial cutouts for receiving commissures of the natural tissue valve leaflets, and concave portions between the cutouts for contacting and biasing the leaflets.

32. A process as in claim 27, wherein the higher pressure is applied to said leaflet base sections by filling a closed space adjacent each base section with a compressible material and compacting the material against the base sections.

33. A process as in claim 27, wherein the natural tissue valve prosthesis includes a natural tubular wall portion extending on the downstream side of the annular margin, and wherein a pressure source is positioned between the tubular member and tubular wall portion to subject the leaflet base sections to the higher pressure.

34. A process as in claim 33, wherein the higher pressure is applied to the leaflet base sections by inflating a bladder positioned outside of the tubular member and inside of the tubular wall portion.

35. A process as in claim 34, further including subjecting the leaflet base sections to an intermittent higher pressure.

36. A process as in claim 27, further comprising mounting the natural tissue valve prosthesis on a surrounding stent support prior to said step of subjecting.

* * * * *